United States Patent [19]

Cornils et al.

[11] Patent Number: 4,532,354

[45] Date of Patent: Jul. 30, 1985

[54] METHOD FOR PURIFYING N,N-DIMETHYLAMINOPROPYLAMINE

[75] Inventors: Boy Cornils, Dinslaken; Ernst Wiebus, Oberhausen; Norbert Breitkopf, Bottrop, all of Fed. Rep. of Germany

[73] Assignee: Ruhrchemie Aktiengesellschaft, Fed. Rep. of Germany

[21] Appl. No.: 379,742

[22] Filed: May 19, 1982

[30] Foreign Application Priority Data

May 23, 1981 [DE] Fed. Rep. of Germany ....... 3120558

[51] Int. Cl.$^3$ ............................................. C07C 85/26
[52] U.S. Cl. ..................................... 564/498; 564/497; 564/499
[58] Field of Search ......................... 564/498, 499, 497

[56] References Cited

U.S. PATENT DOCUMENTS

| | | | |
|---|---|---|---|
| 3,038,904 | 6/1962 | Godfrey | 544/404 X |
| 3,755,447 | 8/1973 | Klemann et al. | 564/461 |
| 3,758,580 | 9/1973 | Lancer et al. | 564/498 |
| 4,055,586 | 10/1977 | Feichtinger et al. | 260/465.5 R |
| 4,172,091 | 10/1979 | Weber et al. | 564/499 X |

FOREIGN PATENT DOCUMENTS 359248  1/1973  U.S.S.R. ............................ 564/498

OTHER PUBLICATIONS

Hares et al., JACS, vol. 78 (1956), pp. 1816–1818.

*Primary Examiner*—Thomas A. Waltz
*Attorney, Agent, or Firm*—Jordan B. Bierman; Linda Bierman

[57] ABSTRACT

The present invention relates to a method for purifying N,N-dimethylaminopropylamine containing 1,3-diaminopropane as an impurity. Dimethylaminopropionitrile is formed by adding dimethylamine to acrylonitrile, and is then converted by subsequent hydrogenation and distillation into N,N-dimethylaminopropylamine. The impurity 1,3-diaminopropane is removed by adding a metal salt of a transition element which forms a stable complex with the 1,3-diaminopropane.

9 Claims, No Drawings

METHOD FOR PURIFYING N,N-DIMETHYLAMINOPROPYLAMINE

This application claims the priority of German application No. P31 20 558.5, filed May 23, 1981.

N,N-dimethylaminopropylamine (N,N-dimethyl-1,3-diaminopropane, 3-dimethylaminopropylamine) is an important intermediate in the large-scale production of pharmaceuticals, surfactants, hardeners for epoxy resins, or ion exchangers, and is also required as a starting product in the production of flocculating agents, road marking paints and polyurethanes.

N,N-dimethylaminopropylamine (DMAPA) is normally produced by reacting acrylonitrile and dimethylamine. Dimethylaminopropionitrile is formed in this addition reaction. A process of this type, namely the reaction of dimethylamine with acrylonitrile in a blow column reactor, is described in German Patent Specification No. 27 09 966.

N,N-dimethylaminopropylamine is obtained by subsequent hydrogenation of the crude product in the gaseous phase or liquid phase. Commercially available supported catalysts based on nickel or cobalt are used as hydrogenation catalysts. During this multi-stage synthesis by-products are formed as a result of competing reactions and secondary reactions, which can react further with the starting products.

Thus, the crude mixture obtained after hydrogenating the dimethylaminopropionitrile essentially contains the following products in addition to the desired N,N-dimethylaminopropylamine: trimethylamine (3° C.), n-propylamine (47.8° C.), allylamine (58° C.), N-methyl-n-propylamine (62.5° C.), N,N-dimethyl-n-propylamine (65.6° C.), propionitrile (97.4° C.), di-n-propylamine (110° C.), N,N,N'-trimethyl-1,3-diaminopropane (138° C.), N-methyl-1,3-diaminopropane (140° C.), N,N,N',N'-tetramethyl-1,3-diaminopropane (145° C.), tri-n-propylamine (156° C.), N-methy-aminopropionitrile (approx. 170° C.), N,N-dimethylaminopropionitrile (177° C.) and N,N,N',N'-tetramethyldipropyleneriamine (241° C.).

The figures in brackets correspond in each case to the boiling point of the relevant substance at 1013 mbars.

The desired main product N,N-dimethylaminopropylamine has a boiling point of 134.8° C. (at 1013 mbars).

On account of the multiplicity of the inevitably produced by-products, the desired N,N-dimethylaminopropylamine necessarily has to be purified. Distillative processing is generally preferred. In this connection, it is found that all the afore-mentioned components can be completely removed by means of an unfortunately expensive but nevertheless practicable distillation process.

However, this is not the case for the component 1,3-diaminopropane which is also contained in the unpurified mixture, and whose boiling point is 136° C. (measured at 1013 mbars). This impurity, which is always present in an amount of about 200 to approx. 5000 ppm in the unpurified mixture, depending on the age of the hydrogenation catalyst, cannot be removed to the desired extent even when using very costly distillation equipment (a large number of trays and a high reflux ratio). Separation of 1,3-diaminopropane is absolutely essential since its presence, even in very small amounts, leads in the subsequent processing to intermediate products not according to specification, or to unallowable opacity or discolouration in the secondary products.

The slight difference between the boiling points of 1,3-diaminopropane and N,N-dimethylaminopropylamine of only about 2° C. at normal pressure is increased of course to approx. 9° C. by distillation in a vacuum at 10 mbars, though even this boiling point difference is not sufficient to separate 1,3-diaminopropane sufficiently so that the N,N-dimethylaminopropylamine only contains residual amounts of less than 100 ppm of 1,3-diaminopropane (referred to N,N-dimethylaminopropylamine) (see comparison experiment 1).

Another technically frequently adopted method for removing impurities from a crude product is to separate the impurities by distillation by adding suitable azeotrope-forming agents and utilising the azeotropes thus formed, and thereby effect a purification.

Corresponding azeotropic data for the compound 1,2-diaminopropane, which is formally similar to 1,3-diaminopropane, is known from the literature. (L.H. Horsley, Azeotropic data, Advances in Chemistry Series No. 116, American Chemical Society (Wash. D.C.), 1973). Azeotropes are formed from 1,2-diaminopropane with i-butanol or toluene. Their boiling points are given as 123° C. and 105° C. respectively. The levels of 1,2-diaminopropane are 65% by weight and 32% by weight respectively. Assuming that 1,3-diaminopropane behaves similarly to 1,2-diaminopropane, the expected reductions in the boiling points compared with the boiling point of N,N-diemthylaminopropylamine of 134.8° C. would be sufficient, with suitable apparatus, to effect a distillative separation.

However, it has been found experimentally that this method of removing 1,3-diaminopropane is also not practicable. The residual levels of 1,3-diaminopropane are always far above the limit regarded as permissible for very pure N,N-dimethylaminopropylamine (see comparison experiment 2, Tables 2 and 3).

The object therefore existed of providing a method for purifying N,N-dimethylaminopropylamine which reduces the residual content of 1,3-diaminopropane to values of less than 100 ppm.

This objective is surprisingly achieved by a method for purifying N,N-dimethylaminopropylamine obtained by addition of dimethylamine to acrylonitrile followed by hydrogenation and distillation, and containing 1,3-diaminopropane as impurity, characterised in that metal compounds of the transition elements of the Periodic System are added before or during the distillation to the product to be purified. By the term transition elements are understood the transition metals of atomic numbers 21 to 80.

These metal compounds may be used in the form of inorganic mineral salts, such as nitrates, chlorides, sulphates, carbonates, in pure form, or as an aqueous solution. Furthermore, it is also possible to use organometallic compounds such as carbonyls, acetyl acetonates or carbonylates.

The amounts of metal compound normally used are 0.5 to 20 moles per mole of 1,3-diaminopropane.

Metal chelates are formed from the added metal compounds and the impurity 1,3-diaminopropane. Despite the extremely drastic conditions prevailing in a distillation, these chelates are so heat stable that the complexes once formed have practically no tendency to split into their starting components. The level of 1,3-diaminopropane in N,N-dimethylpropylamine occurring as the head product of a distillation can be reduced very simply to values below 100 ppm by this method.

Metals that may be used in particular include: cobalt, nickel, chromium, iron, manganese, copper, cadmium, as well as zinc or mercury (see Example 1).

The new procedure according to the invention is found to be advantageous in practice, and in particular enables the purification to be carried out with low energy expenditure for the distillation as a result of the low reflux ratios.

On the one hand the metal salt may be arranged in the form of tablets in a fixed bed reactor, through which the crude product flows before being used in the distillation, and on the other hand it is possible to feed an aqueous metal salt solution directly to the bottom of a distillation column in order to achieve the desired purification effect. Both possibilities are covered by the following Examples 2 and 3.

The use of nickel compounds, in particular nickel sulphate, is particularly suitable and, on account of the comparatively low cost, is also of economic interest.

COMPARISON EXAMPLE 1

2000 g of N,N-dimethylaminopropylamine is subjected to fractional discontinuous distillation. The column used has 80 theoretical plates (packed column). Fractions of in each case 10% by weight are withdrawn and investigated for their content of 1,3-diaminopropane. The level of 1,3-diaminopropane in the feedstock (N,N-dimethylaminopropylamine crude product) is 1400 ppm.

The reflux ratio is adjusted to 20 parts reflux per part of withdrawn head product. The level of 1,3-diaminopropane is measured by gas chromatography.

As can be seen from Table 1, there is no significant concentration of 1,3-diaminopropane in the tail fraction, as would have been expected on account of the higher boiling point.

TABLE 1

| Fraction | Temperature of the head product | Temperature of the bottom of the column | Reflux ratio | Pressure (mbars) | Level of 1,3-diaminopropane in ppm |
|---|---|---|---|---|---|
| 1 | 133 | 136 | 20:1 | 1013 | 1500 |
| 2 | 134 | 137 | 20:1 | 1013 | 1400 |
| 3 | 134 | 138 | 20:1 | 1013 | 1800 |
| 4 | 134 | 137 | 20:1 | 1013 | 1400 |
| 5 | 134 | 138 | 20:1 | 1013 | 1400 |
| 6 | 134 | 137 | 20:1 | 1013 | 1300 |
| 7 | 134 | 137 | 20:1 | 1013 | 1400 |
| 8 | 134 | 140 | 20:1 | 1013 | 1400 |
| 9 | 134 | 140 | 20:1 | 1013 | 1400 |
| 10 | 134 | 140 | 20:1 | 1013 | 1400 |

COMPARISON EXAMPLE 2

750 g of toluene and 750 g of i-butanol are added to two batches each of 500 g of N,N-dimethylaminopropylamine and subjected to a fractional discontinuous distillation. The laboratory column used has 40 theoretical plates (packed column). Fractions each of 10% by weight are withdrawn and investigated for their level of 1,3-diaminopropane. The level of 1,3-diaminopropane in the feedstock (N,N-dimethylaminopropylamine crude product) is 1400 ppm.

The reflux ratio is adjusted to 10 parts of reflux per part of withdrawn head product. The level of 1,3-diaminopropane is measured by gas chromatography.

As can be seen from Tables 2 and 3, there is no significant concentration of 1,3-diaminopropane as an azeotrope with the first runnings from toluene or i-butanol; the main fraction of N,N-dimethylaminopropylamine passing over after separating the first runnings contains approx. 1400 ppm of 1,3-diaminopropane.

Table 2 gives the results using toluene, and Table 3 the results using i-butanol.

TABLE 2

| | (Toluene Addition) | | | | |
|---|---|---|---|---|---|
| Fraction | Temperature of the head product | Temperature of the bottom of the column | Reflux ratio | Pressure (mbars) | Level of 1,3-diaminopropane in ppm |
| 1* | 111 | 122 | 10:1 | 1013 | 50 |
| 2* | 111 | 124 | 10:1 | 1013 | 50 |
| 3* | 111 | 124 | 10:1 | 1013 | 50 |
| 4* | 111 | 129 | 10:1 | 1013 | 50 |
| 5* | 112 | 134 | 10:1 | 1013 | 50 |
| 6** | 135 | 137 | 10:1 | 1013 | 700 |
| 7 | 135 | 138 | 10:1 | 1013 | 1300 |
| 8 | 135 | 138 | 10:1 | 1013 | 1400 |
| 9 | 135 | 160 | 10:1 | 1013 | 1300 |
| 10 | 133 | 220 | 10:1 | 1013 | 1000 |

*Toluene level >99%
**Toluene level approx. 50%

TABLE 3

| | (i-butanol Addition) | | | | |
|---|---|---|---|---|---|
| Fraction | Temperature of the head product | Temperature of the bottom of the column | Reflux ratio | Pressure (mbars) | Level of 1,3-diaminopropane in ppm |
| 1* | 108 | 110 | 10:1 | 1013 | <100 |
| 2* | 108 | 113 | 10:1 | 1013 | <100 |
| 3* | 108 | 117 | 10:1 | 1013 | <100 |

TABLE 3-continued

| | | (i-butanol Addition) | | | |
|---|---|---|---|---|---|
| Fraction | Temperature of the head product | Temperature of the bottom of the column | Reflux ratio | Pressure (mbars) | Level of 1,3-diaminopropane in ppm |
| 4* | 108 | 117 | 10:1 | 1013 | <100 |
| 5* | 108 | 128 | 10:1 | 1013 | <100 |
| 6* | 132 | 139 | 10:1 | 1013 | <100 |
| 7 | 134 | 140 | 10:1 | 1013 | 1500 |
| 8 | 135 | 140 | 10:1 | 1013 | 1300 |
| 9 | 135 | 140 | 10:1 | 1013 | 1500 |
| 10 | 134 | 180 | 10:1 | 1013 | 1200 |

*Isobutanol level >99%

EXAMPLE 1

800 g of N,N-dimethylaminopropylamine crude product containing 220 ppm of 1,3-diaminopropane is added to a 2 liter three-necked flask equipped with a reflux condenser, stirrer and internal thermometer and, per experiment, 1% by weight of copper carbonate or iron (III) sulphate or basic chromium sulphate or cobalt carbonate is added, and the contents are heated to 70° C. under intensive stirring and kept for 6 hours at this temperature. The N,N-dimethylaminopropylamine is then freed by flashing from excess metal salt and the chelate complex. The level of 1,3-diaminopropane in the flashed N,N-dimethylaminopropylamine is shown in the following Table 4. The crude product is further purified by fractional distillation.

TABLE 4

| Salt used | Level of 1,3-diaminopropane (ppm) |
|---|---|
| Copper carbonate | 80 |
| Iron (III) sulphate | 70 |
| Basic chromium sulphate | 95 |
| Cobalt (II) carbonate | 65 |

EXAMPLE 2

A cylindrical 500 ml volume glass vessel is filled with nickel sulphate pellets. The vessel is externally heated to 120° C. and kept constant at this temperature. 100 ml of N,N-dimethylaminopropylamine containing 1400 ppm of 1,3-diaminopropane is passed upwardly per hour through this fixed bed packing.

The N,N-dimethylaminopropylamine leaving the head of the reaction tube has a level of approx. 80 ppm of 1,3-diaminopropane. Further purification is carried out by fractional distillation.

EXAMPLE 3

In the continuous distillative processing of N,N-dimethylaminopropylamine crude product, nickel sulphate (NiSo$_4$.7H$_2$O) in the form of a 25% aqueous solution is added to the bottom of the column during the separation of the low boiling first runnings. 1.5 mole of nickel sulphate is added per mole of 1,3-diaminopropane. The temperature of the bottom of the column is approx. 140° C., and the average residence time of the product mixture in the bottom of the column is approx. 1 hour.

The addition of nickel sulphate reduces the 1,3-diaminopropane level from an original value of approx. 300 ppm to a residual value of only approx. 30 ppm.

What we claim is:

1. A method for purifying N,N-dimethylaminopropylamine obtained by reacting dimethylamine and acrylonitrile to form a first product; hydrogenating said first product to form a second product containing said N,N-dimethylaminopropylamine and, as a contaminent thereof, 1,3-diaminopropane; and distilling said second product; comprising
    adding a compound of a transition metal to said second product in an amount of about 0.5 to about 20 moles per mole of said 1,3-diaminopropane contaminent either before or during said distillation step; and said distillation of said second product taking place in the presence of said compound.

2. The method of claim 1 wherein said transition metal is selected from the group consisting of cobalt, nickel, chromium, iron, manganese, copper, cadmium, zinc and mercury.

3. The method of claim 1 or 2 wherein said compound of a transition metal is a transition metal salt selected from the group consisting of transition metal chloride, sulfate, carbonate, and nitrate, or an organo metallic compound of a transition metal containing an organic portion selected from the group consisting of carbonyls, acetyl acetonates and carbonylates.

4. The method of claim 1 wherein said transition metal is nickel.

5. The method of claim 3 wherein said transition metal is nickel.

6. The method of claim 1 wherein said transition metal compound is nickel sulfate (NiSO$_4$).

7. The method of claim 1, 2, 4 or 6 wherein said transition metal compound is arranged in the form of a fixed bed or is fed as an aqueous solution directly to the bottom of a distillation column in which said distillation step takes place.

8. The method of claim 3 wherein said transition metal compound is arranged in the form of a fixed bed or is fed as an aqueous solution directly to the bottom of a distillation column in which said distillation step takes place.

9. The method of claim 5 wherein said transition metal compound is arranged in the form of a fixed bed or is fed as an aqueous solution directly to the bottom of a distillation column in which said distillation step takes place.

* * * * *